(12) United States Patent
Jaatinen et al.

(10) Patent No.: US 7,637,747 B2
(45) Date of Patent: Dec. 29, 2009

(54) CONNECTOR MECHANISM

(75) Inventors: Jukka Jaatinen, Kempele (FI); Hans Bauer, Balingen (DE)

(73) Assignee: Polar Electro Oy, Kempele (FI)

( * ) Notice: Subject to any disclaimer, the term of this patent is extended or adjusted under 35 U.S.C. 154(b) by 411 days.

(21) Appl. No.: 11/650,850

(22) Filed: Jan. 8, 2007

(65) Prior Publication Data

US 2007/0177298 A1 Aug. 2, 2007

(30) Foreign Application Priority Data

Jan. 31, 2006 (FI) ................... 20065069

(51) Int. Cl.
*H01R 11/30* (2006.01)
(52) U.S. Cl. .............. 439/39; 607/60; 607/2; 600/561
(58) Field of Classification Search ............ 439/39, 439/38; 607/60, 2; 600/561
See application file for complete search history.

(56) References Cited

U.S. PATENT DOCUMENTS

| | | | |
|---|---|---|---|
| 3,521,216 A * | 7/1970 | Tolegian | 439/39 |
| 3,786,391 A * | 1/1974 | Mathauser | 439/39 |
| 4,025,964 A * | 5/1977 | Owens | 623/11.11 |
| 4,067,342 A | 1/1978 | Burton | |
| 4,653,503 A | 3/1987 | Heath | |
| 5,507,303 A | 4/1996 | Kuzma | |
| 5,779,487 A | 7/1998 | Gatin | |
| 5,781,511 A | 7/1998 | Yasukawa et al. | |
| 6,736,646 B2 * | 5/2004 | Takahashi et al. | 439/39 |
| 7,344,379 B2 * | 3/2008 | Marmaropoulos et al. | 439/37 |
| 7,344,380 B2 * | 3/2008 | Neidlein et al. | 439/39 |
| 2001/0031565 A1 | 10/2001 | Koji | |
| 2002/0182898 A1 * | 12/2002 | Takahashi et al. | 439/39 |
| 2003/0114032 A1 | 6/2003 | Koji | |
| 2005/0096554 A1 | 5/2005 | Dudik et al. | |
| 2005/0239261 A1 | 10/2005 | Tai et al. | |

FOREIGN PATENT DOCUMENTS

| | | |
|---|---|---|
| DE | 29 23 663 | 12/1980 |
| EP | 0653182 | 5/1995 |
| EP | 1 143 310 A2 | 10/2001 |
| JP | 05032755 | 2/1993 |
| JP | 07111178 | 4/1995 |
| JP | 10189168 | 7/1998 |
| WO | WO 2004/066400 | 8/2004 |
| WO | WO 2004/095647 | 11/2004 |
| WO | WO 2005/101582 | 10/2005 |

* cited by examiner

*Primary Examiner*—Gary F. Paumen
(74) *Attorney, Agent, or Firm*—Hoffmann & Baron, LLP

(57) ABSTRACT

The invention relates to a connector mechanism, a connector, an electronic device, a garment and a physiological sensor. The connector mechanism comprises a first connector part, which includes a first electrically conductive layer and a first magnetic layer, and a second connector part, which includes a second electrically conductive layer and a second magnetic layer, the first and the second magnetic layers being configured to provide a mechanical coupling between the first connector part and the second connector part based on the mutual magnetic attraction between the first and the second magnetic layers, and the first electrically conductive layer and the second electrically conductive layer being configured to provide an electrical connection between the first connector part and the second connector part based on said mutual magnetic attraction.

20 Claims, 3 Drawing Sheets

CONNECTOR MECHANISM

CROSS-REFERENCE TO RELATED APPLICATION

This application claims priority to Finnish Patent Application Serial No. 20065069, filed on Jan. 31, 2006, which is incorporated herein by reference.

BACKGROUND OF THE INVENTION

1. Field of the Invention

The invention relates to a connector mechanism, a connector, an electronic device, a garment and a physiological sensor.

2. Description of the Related Art

Electronic devices often include electronic components that may be mechanically and electrically coupled to one another or detached from one another. Mechanical coupling physically engages the electronic components in a desired manner and electrical connection enables exchange of electric signals between the components.

In prior art, electronic components may be interconnected with mechanical quick-couplers, such as various latching mechanisms. Electrical connections may be carried out, for instance, by coupling wires to wire adapters.

Prior art solutions have drawbacks that mechanical quick-couplers and wire adapters are difficult to use and their working reliability is poor. Therefore, it is useful to search for other approaches to implement connector mechanisms.

SUMMARY OF THE INVENTION

The object of the invention is to provide a connector mechanism, a connector, an electronic device, a garment and a physiological sensor for achieving a user-friendly mechanical and electrical connection of electronic components.

A first aspect of the invention is a connector mechanism comprising: a first connector part, which includes a first electrically conductive layer and a first magnetic layer, and a second connector part, which includes a second electrically conductive layer and a second magnetic layer, the first and the second magnetic layers being configured to provide a mechanical coupling between the first connector part and the second connector part based on the mutual magnetic attraction between the first and the second magnetic layers, and the first and the second electrically conductive layers being configured to provide an electrical connection between the first and the second connector parts based on said mutual magnetic attraction.

A second aspect of the invention is a connector comprising: a first connector part, which includes a first electrically conductive layer and a first magnetic layer, the first magnetic layer being configured to provide a mechanical coupling between the first and the second connector parts based on the mutual magnetic attraction between the first magnetic layer and the magnetic layer of the second connector part, and the first electrically conductive layer being configured to provide an electrical connection between the first electrically conductive layer and the electrically conductive layer of the second connector part based on said mutual magnetic attraction.

A third aspect of the invention is an electronic device comprising: a first electronic component, which includes a first electrically conductive layer and a first magnetic layer, and a second electronic component, which includes a second electrically conductive layer and a second magnetic layer, the first and the second magnetic layers being configured to provide a mechanical coupling between the first electronic component and the second electronic component based on the mutual magnetic attraction between the first and the second magnetic layers, and the first and the second electrically conductive layers being configured to provide an electrical connection between the first connector part and the second connector part based on said mutual magnetic attraction.

A fourth aspect of the invention is an electronic device comprising: a first electronic component, which includes a first electrically conductive layer and a first magnetic layer, the first magnetic layer being configured to provide a mechanical coupling between a first connector part and the second connector part of the second electronic component based on the mutual magnetic attraction between the first magnetic layer and the magnetic layer of the second connector part of the second electronic component, and the first electrically conductive layer being configured to provide an electrical conection between the first electrically conductive layer and the electrically conductive layer of the second electronic component based on said mutual magnetic attraction.

A fifth aspect of the invention is a garment comprising a connector for coupling the garment mechanically and electrically, the connector comprising: a first connector part, which includes a first electrically conductive layer and a first magnetic layer, the first magnetic layer being configured to provide a mechanical coupling between the first connector part and the second connector part based on the mutual magnetic attraction between the first magnetic layer and the magnetic layer of the second connector part, and the first electrically conductive layer being configured to provide an electrical connection between the first electrically conductive layer and the electrically conductive layer of the second connector part based on said mutual magnetic attraction.

Another aspect of the invention is a physiological sensor comprising a connector for coupling the physiological sensor mechanically and electrically, the connector comprising: a first connector part, which includes a first electrically conductive layer and a first magnetic layer, the first magnetic layer being configured to provide a mechanical coupling between the first connector part and the second connector part based on the mutual magnetic attraction between the first magnetic layer and the magnetic layer of the second connector part, and the first electrically conductive layer being configured to provide an electrical connection between the first electrically conductive layer and the electrically conductive layer of the second connector part based on said mutual magnetic attraction.

The preferred embodiments of the invention are disclosed in dependent claims.

The invention is based on the idea that both the first connector part and the second connector part include a magnetic layer and an electrically conductive layer. The magnetic properties of the magnetic layers are selected such that as the connector parts are set one against the other the magnetic layers attract each other, whereby a mechanical coupling is provided between the connector parts, the coupling holding the connector parts together. At the same time the electrically conductive layers are pressed against one another between the connector parts, whereby an electric contact will be provided between the electrically conductive layers, which enables transmission of electric signals from one connector part to the other. Thus, the invention provides a mechanism, in which the connector parts may be readily coupled to one another and detached from one another mechanically and electrically.

BRIEF DESCRIPTION OF THE DRAWINGS

In the following, the invention will be described in greater detail in connection with preferred embodiments, with reference to the attached drawings, in which.

DETAILED DESCRIPTION OF THE PREFERRED EMBODIMENTS

Figure 1:
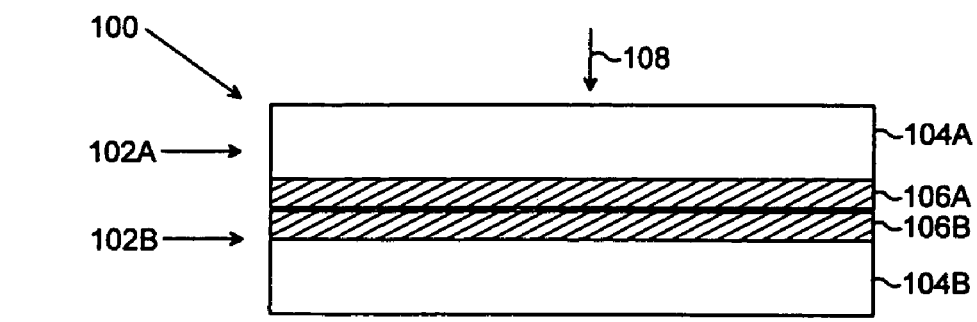
FIG. 1 shows an example of the structure of a preferred embodiment of a connector mechanism.

With reference to FIG. 1, a connector mechanism 100 comprises a first connector part 102A and a second connector part 102B. The first connector part 102A includes a first electrically conductive layer 106A and in connection with the first electrically conductive layer 106A a first magnetic layer 104A.

A second connector part 102B includes a second electrically conductive layer 106B and in connection with the second electrically conductive layer 106B a second magnetic layer 104B.

The magnetic properties of the first magnetic layer 104A and the second magnetic layer 104B may be mutually arranged such that as the first connector part 102A and the second connector part 102B are set one against the other with the electrically conductive layers 106A, 106B facing each other, the mutual magnetic attraction 118 between the first magnetic layer 104A and the second magnetic layer 104B draws the first connector part 102A and the second connector part 102B together. Thus, between the first connector part 102A and the second connector part 102B there is provided a mechanical coupling that holds the first connector part 102A and the second connector part 102B mutually engaged. At the same time, the first electrically conductive layer 106A and the second electrically conductive layer 106B are sandwiched between the first magnetic layer 104A and the second magnetic layer 104B, whereby between the first electrically conductive layer 106A and the second electrically conductive layer 106B there is provided an electrical connection that enables propagation of electric signals between the first electrically conductive layer 106A and the second electrically conductive layer 106B.

The magnetic compatibility of the first magnetic layer 104A and the second magnetic layer 104B may be achieved in a variety of ways.

In one embodiment the first magnetic layer 106A and the second magnetic layer 106B comprise permanent magnets, the polarity of which is selected such that mutual magnetic attraction 108 is provided between the first magnetic layer 106A and the second magnetic layer 106B.

In one embodiment the first magnetic layer 106A comprises a permanent magnet and the second magnetic layer 106B comprises magnetable material, In one embodiment the second magnetic layer 106B comprises a permanent magnet and the first magnetic layer 106A comprises magnetable material.

The magnetable material is magnetized in the magnetic field of the permanent magnet, whereby mutual magnetic attraction 108 will be provided between the permanent magnet and the magnetable material.

The permanent magnet may contain premagnetized, ferromagnetic material, such as premagnetized iron, nickel or cobalt or any magnetized material having high magnetic permeability and magnetic hysteresis.

The magnetable material may contain non-premagnetized or weakly premagnetized ferromagnetic material such as iron, nickel and/or cobalt.

The first electrically conductive layer 106A may be made of metal, metallic fibre structure, conductive polymer or any conductive material that allows layer formation.

The second electrically conductive layer 106B may be made of metal, metallic fibre structure, conductive polymer or any conductive material that allows layer formation.

The metal may be, for instance, copper, aluminium and/or silver.

The metallic fibre structure may be, for instance, gold- or silver-plated fabric.

The conductive polymer may be, for instance, conductive plastic film.

Figure 2:
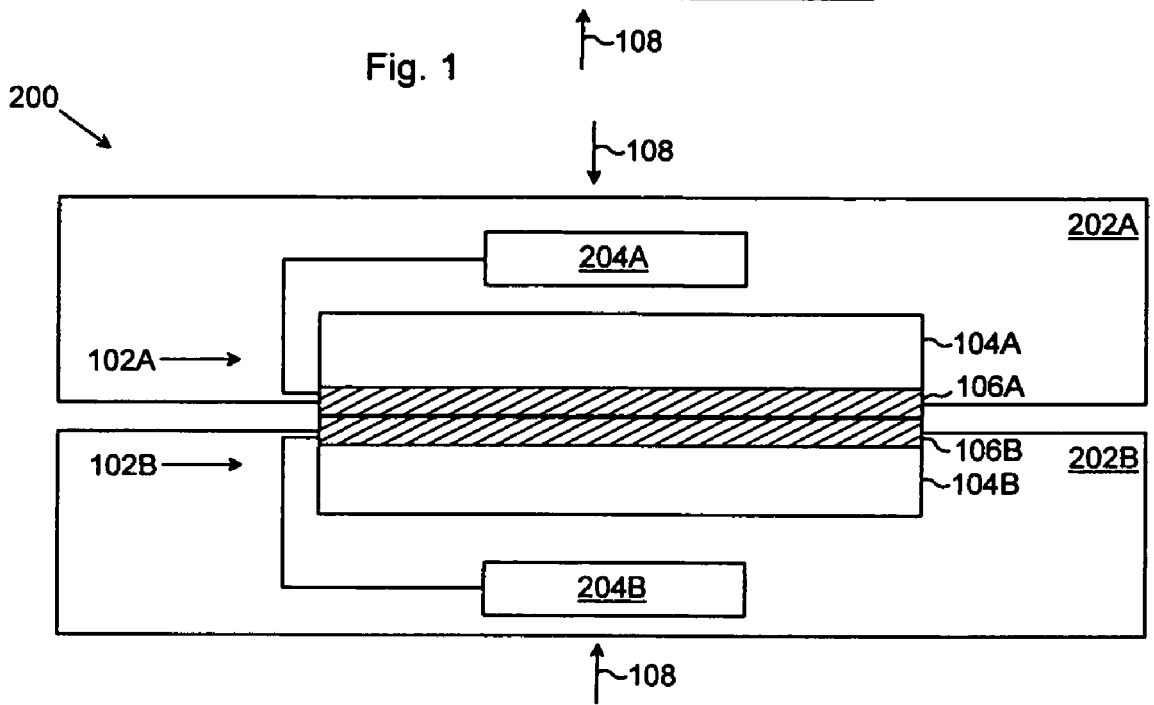
FIG. 2 shows a first example of an embodiment of an electronic device.

With reference to FIG. 2, we now examine an electronic device 200 in accordance with one embodiment of the disclosed solution, which device may be, for instance, a part of a performance measuring system. The electronic device 200 comprises a first electronic component 202A and a second electronic component 202B.

The first electronic component 202A comprises a first operational unit 204A for performing an operation of the electronic device 200. The second electronic component 202B comprises a second operational unit 204B for performing an operation of the electronic device 200. The operation may be signal transmission, signal processing, signal amplification or any event □ttracting the signal.

The performance measuring system is typically a system comprising electronic devices which record performance information relating to the user's performance, such as physical exercise. The electronic devices may be attachable to the user's body or external devices separate from the user.

In one embodiment the first electronic component 202A is a measuring sensor and the second electronic component 202B is a signal conductor to be connected to the measuring sensor, a processing unit, a transmitter unit, a measuring sensor control unit or any part of the performance measuring system that exchanges signals with the measuring sensor. For instance, the measuring sensor is an electrode, a physiological sensor, a temperature sensor, a movement sensor or any sensor in the performance measuring system.

In one embodiment the first electronic component 202A is a peripheral device in the performance measuring system and the second electronic component 202B is a signal conductor to be connected to the peripheral device, a processing unit, a transmitter unit, a peripheral device control unit or any part of the performance measuring system that exchanges signals with the peripheral device. For instance, the peripheral device may be a satellite positioning device.

The performance information is typically information relating to the user's performance, such as physiological data measured on the user, information associated with the performance environment and/or information controlling the performance.

The first connector part 102A is coupled electrically and mechanically to the first electronic component 202A and the second connector part 102B is coupled electrically and mechanically to the second electronic component 202B. Thus, the interconnected first connector part 102A and the second connector part 102B couple the first electronic component 102A and the second electronic component 202B electrically and mechanically to one another. This enables the exchange of electrical signals between the first operational unit 204A and the second operational unit 204B.

Figure 3:
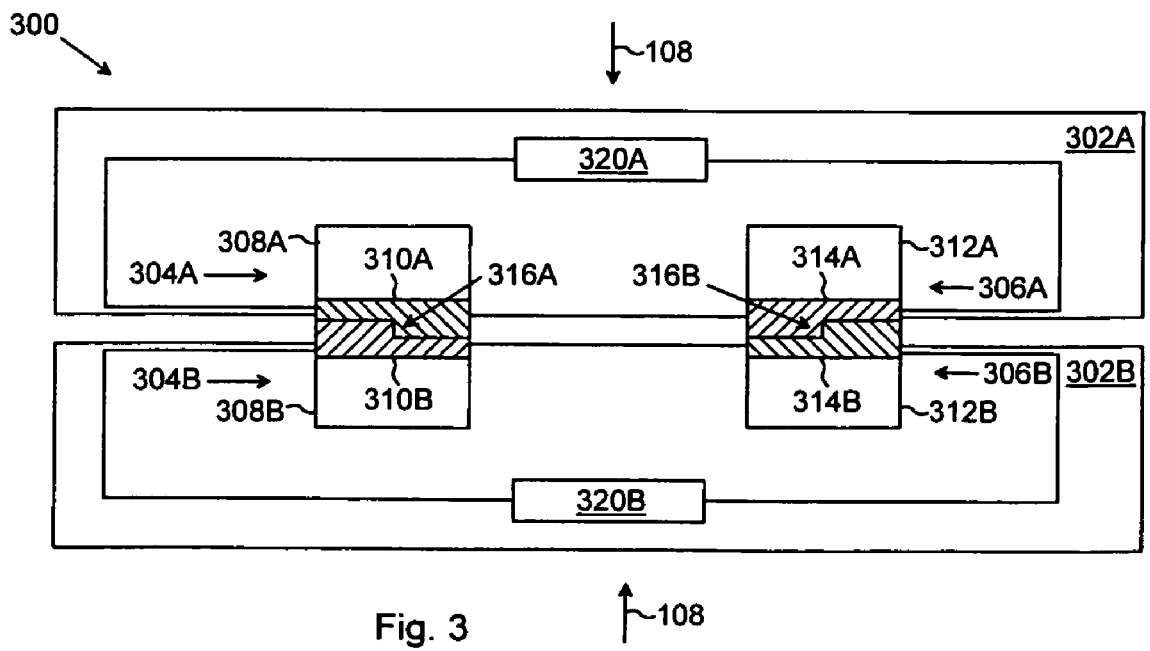
FIG. 3 shows a second example of an embodiment of the electronic device.

With reference to the example of FIG. 3, the electronic device 300 comprises a plurality of first connector parts 304A, 306A coupled to a first electronic component 302A and a plurality of second connector parts 304B and 306B coupled to a second electronic component 302B.

The first connector part 304A, 306A includes a plurality of first magnetic layers 308A, 312A and a plurality of first electrically conductive layers 310A, 314A in connection with the first magnetic layers 308A, 312A.

The first electrically conductive layers 310A, 314A may be coupled to a first operational unit 320A.

The second connector part 304B, 306B includes a plurality of second magnetic layers 308B, 312B and a plurality of second electrically conductive layers 310B, 314B in connection with the second magnetic layers 308B, 312B.

The second electrically conductive layers 310B, 314B may be coupled to a second operational unit 320B.

In one embodiment the connector mechanism comprises a positioning structure 316A, 316B for mutual positioning of the first connector part 304A, 306A and the second connector part 304B, 306B. The positioning structure 316A, 316B may restrict the lateral movement between the first connector part 304A, 306A and the second connector part 304B, 306B and positions the first electrically conductive layer 310A, 314A and the second electrically conductive layer 310B, 314B in relation to one another.

The positioning structure 316A, 316B may be implemented, for instance, by designing the first connector part 304A, 306A and the second connector part 304B, 306B mutually such that the lateral movement between the first connector part 304A, 306A and the second connector part 304B, 306B will be restricted or prevented. The design may comprise a notch structure as shown in FIG. 3.

Figure 4A:
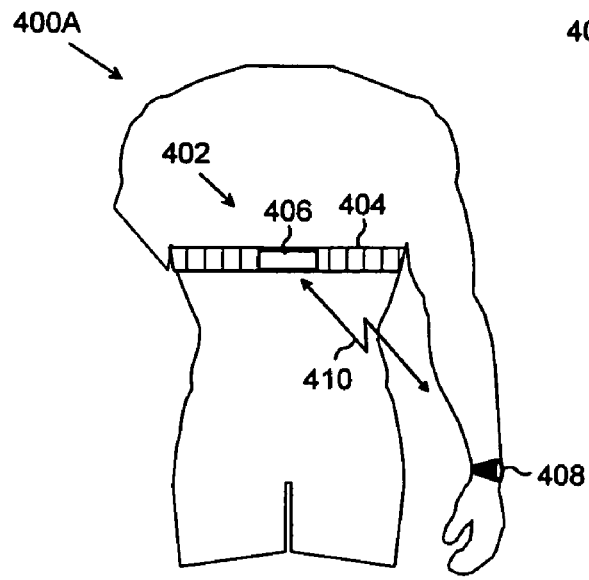
FIG. 4A is a third example of an embodiment of the electronic device.

With reference to FIG. 4A, there is given an example of the structure of the performance measuring system. The performance measuring system typically comprises at least one measuring unit 402 and a central unit 408 which may communicate with the measuring unit 402 over a wireless link 410 or by means of a conductor arrangement integrated in the garment. In the given example the measuring unit 402 is an ECG measuring unit which comprises a heart rate transmitter 406 and a physiological sensor 4040 to be attached to the user, such as a heart rate sensor 404.

The heart rate sensor 404 typically comprises an elastic frame part and electrodes integrated in the elastic frame part, which electrodes are in electric contact with the user's 400A thoracic area.

In one embodiment the connector mechanism is applied to providing a mechanical and an electrical coupling between the heart rate transmitter 406 and the physiological sensor 404. In that case the first connector part 304A, 306A of FIG. 3 may constitute a part of the heart rate transmitter 406 and the second connector part 304B, 306B may constitute a part of the heart rate sensor 404. In the presented embodiment the connector mechanism enables quick and easy attachment and detachment between the heart rate transmitter 406 and the heart rate sensor 404.

Figure 4B:
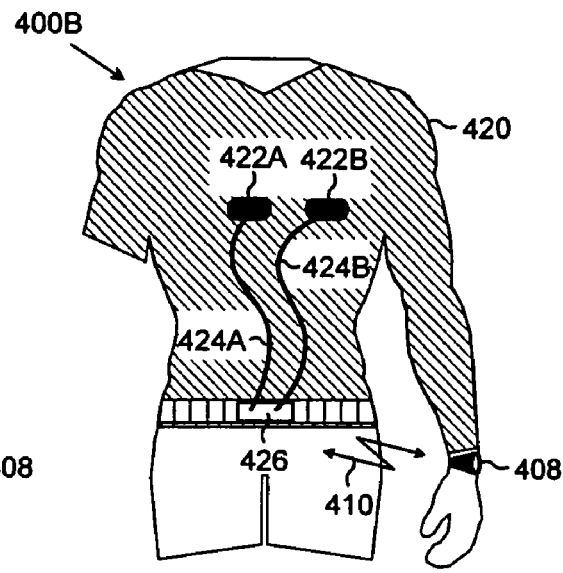
FIG. 4B is a fourth example of an embodiment of the electronic device.

With reference to FIG. 4B, in connection with the garment, the connector mechanism may be applied to providing a mechanical and an electrical connection between the electrodes 422A, 422B attached to the user 400B and the heart rate transmitter 426. The electrodes 422A, 422B may be separate or integrated in the garment 420. The first connector part 102A of FIG. 1 may be coupled to the conductor 424A, 424B of the electrode 422A, 422B and the second connector part 102B may be coupled to the heart rate transmitter 426. In the presented embodiment the connector mechanism enables quick and easy attachment and detachment between the conductor 424A, 424B and the heart rate transmitter 426.

Figure 5:
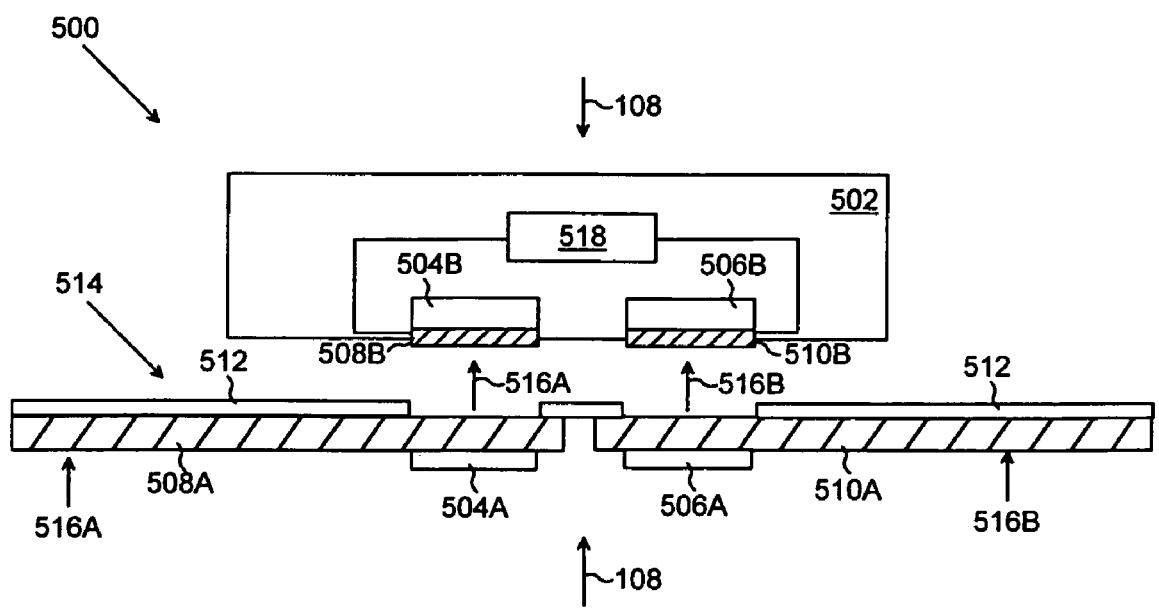
FIG. 5 is a fifth example of an embodiment of the electronic device and FIG. 6 is a sixth example of an embodiment of the electronic device.

With reference to the example in FIG. 5, in one embodiment the electronic device 500 comprises a physiological sensor 514 for detecting a physiological signal 516A, 516B in the user's body and a processing unit 502 for processing the physiological signal 516A, 516B.

The physiological sensor 514 comprises first electrically conductive layers 508A, 510A which transmit the physiological signal 516A, 516B from the physiological sensor 514 to second electrically conductive layers 508B, 510B of the processing unit 502. The second electrically conductive layers may be connected to an electronic circuit 518 of the processing unit 502. The electronic circuit 518 is, for instance, a processor, a transmitter unit or any electronic circuit that processes the physiological signal 516A, 516B in one way or the other.

In one embodiment the physiological sensor is a strap-like sensor structure, which may be called a sensor strap, that is fitted on the user's thorax and that detects the user's electrocardiogram.

In one embodiment the first electrically conductive layer 508A, 510A serves as an electrode that is in contact with the user's body and detects an electrocardiogram signal in the user's body, for instance. The first electrically conductive layer 508A, 510A is made of metallic fibre structure, such as silver-plated fabric, for instance. The electrode intended for the detection of the electrocardiogram is typically attached to an attachment structure 512 to be fitted around the user's body, as the heart rate monitor strap 404 of FIG. 4A.

FIG. 5 also shows the first magnetic layers 504A, 506A in connection with the attachment structure 512 and the second magnetic layers 504B, 506B coupled to the processing unit 502. The mutual magnetic ☐ttracttion 108 between the first magnetic layers 504A, 506A and the second magnetic layers 504B, 506B engages the processing unit 502 with the physiological sensor 514, whereby the electrical connection between the first electrically conductive layers 508A, 510A and the second electrically conductive layers 508B, 510B connects the electrodes to the electronic circuit 518.

Figure 6:
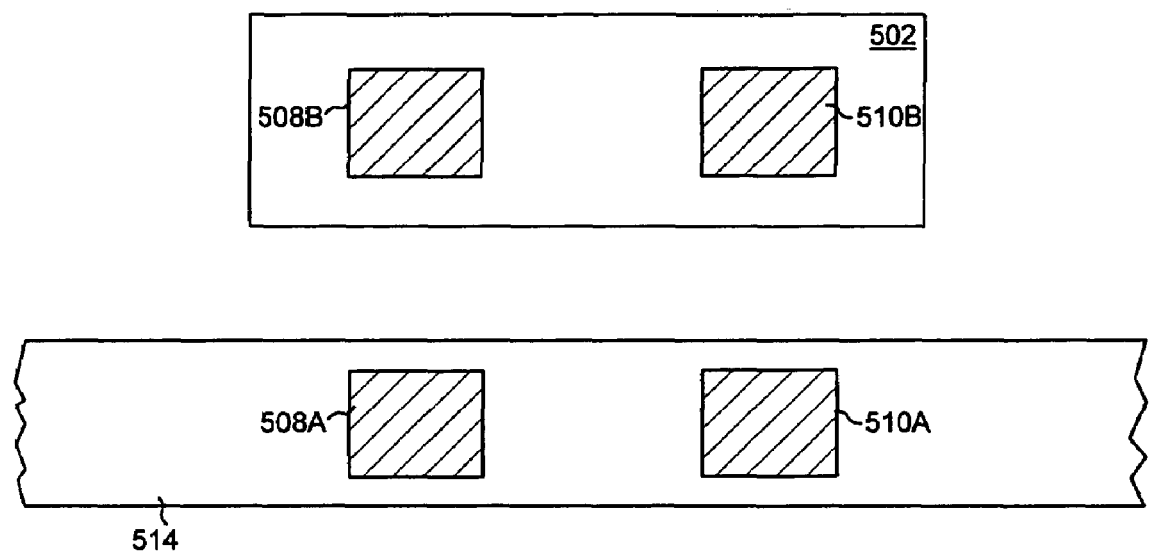

FIG. 6 shows the processing unit 502 and the physiological sensor 514 in the direction of the electrically connecting surfaces.

The first electrically conductive layers 508A, 510A may be passed through the support structure of the sensor 514 in FIG. 5, for instance, by means of through holes. The second electrically conductive layers 508B, 510B may be protrusions that extend through the through holes to the first electrically conductive layers 508A, 510A.

Even though the invention is described above with reference to the example appearing in the attached drawings, it is apparent that the invention is not restricted thereto, but it may be modified in a variety of ways within the scope of the accompanying claims.

What is claimed is:

1. A connector mechanism, comprising:

a first connector part coupled electrically and mechanically to a first electronic component, the first connector part including a first electrically conductive layer and a first magnetic layer; and a second connector part coupled electrically and mechanically to a second electronic component, the second connector part including a second electrically conductive layer and a second magnetic layer, the first and the second magnetic layers being configured to provide a mechanical coupling between the first connector part and the second connector part based on the mutual magnetic attraction between the first and the second magnetic layers, and the first and the second electrically conductive layers being configured to provide an electrical connection between the first and the second connector parts based on said mutual magnetic attraction, thereby connecting the first electronic component and the second electronic component electrically and mechanically, wherein the first electronic component is a physiological sensor of a performance measuring system for detecting a physiological signal in the user's body, the second electronic component is a heart rate transmitter of the performance measuring system, wherein the heart rate transmitter is configured to establish a wireless link for transmitting information, wherein the first electrically conductive later is configured to transfer the physiological signal from the physiological sensor to the second electrically conductive layer and the second electrically conductive layer is configured to transfer the physiological signal to the heart rate transmitter; or wherein the first electronic component is a heart rate transmitter of a performance measuring system, wherein the heart rate transmitter is configured to establish a wireless link for transmitting information, wherein the second electronic component is a physiological sensor of a performance measuring system for detecting the physiological signal in the user's body, wherein the second electrically conductive layer is configured to transfer the physiological signal from the physiological sensor to the first electrically conductive layer and the first electrically conductive layer is configured to transfer the physiological signal to the heart rate transmitter.

2. The connector mechanism of claim 1, wherein the first electrically conductive layer and the second electrically conductive layer are configured for being sandwiched between the first magnetic layer and the second magnetic layer.

3. The connector mechanism of claim 1, further comprising a positioning structure for mutual positioning of the first connector part and the second connector part.

4. The connector mechanism of claim 1, wherein the first electrical component is a heart rate sensor comprising an elastic frame part and electrodes integrated in the elastic frame part, the electrodes being configured to be in electric contact with the user's thoracic area.

5. A connector comprising:

a first connector part coupled electrically and mechanically to a first electronic component, the first connector part including a first electrically conductive layer and a first magnetic layer, the first magnetic layer being configured to provide a mechanical coupling between the first connector part and a second connector part based on the mutual magnetic attraction between the first magnetic layer and the magnetic layer of the second connector part, the second connector part being coupled electrically and mechanically to a second electronic component, the first electrically conductive layer being configured to provide an electrical connection between the first electrically conductive layer and an electrically conductive layer of the second connector part based on said mutual magnetic attraction, thereby connecting the first electronic component and the second electronic component electrically and mechanically, wherein the first electronic component is a physiological sensor of a performance measuring system for detecting a physiological signal in the user's body, the second electronic component is a heart rate transmitter of the performance measuring system, wherein the heart rate transmitter is configured to establish a wireless link for transmitting information, wherein the first electrically conductive layer is configured to transfer the physiological signal from the physiological sensor to the second electrically conductive layer and the second electrically conductive layer is configured to transfer the physiological signal to the heart rate transmitter; or wherein the first electronic component is a heart rate transmitter of a performance measuring system, wherein the heart rate transmitter is configured to establish a wireless link for transmitting information, wherein the second electronic component is a physiological sensor of a performance measuring system for detecting the physiological signal in the user's body, wherein the second electrically conductive layer is configured to transfer the physiological signal from the physiological sensor to the first electrically conductive layer and the first electrically conductive layer is configured to transfer the physiological signal to the heart rate transmitter.

6. The connector of claim 5, wherein the first electrically conductive layer is configured for being sandwiched between the first magnetic layer and the second connector part.

7. The connector of claim 5, further comprising a positioning structure for mutual positioning of the first connector part and the second connector part.

8. The connector of claim 5, wherein the first electrical component is a heart rate sensor comprising an elastic frame part and electrodes integrated in the elastic frame part, the electrodes being configured to be in electric contact with the user's thoracic area.

9. An electronic device comprising:

a first electronic component, which includes a first electrically conductive layer and a first magnetic layer, the first electrically conductive layer being coupled electrically and mechanically to the first electronic component; and a second electronic component, which includes a second electrically conductive layer and a second magnetic layer, the second electrically conductive layer being coupled electrically and mechanically to the second electronic component, wherein the first and the second magnetic layers are configured to provide a mechanical coupling between the first electronic component and the second electronic component based on the mutual magnetic attraction between the first and the second magnetic layers; and wherein the first and the second electrically conductive layers are configured to provide an electrical connection between the first connector part and the second connector part based on said mutual magnetic attraction, thereby connecting the first electronic component and the second electronic component electrically and mechanically, wherein the first electronic component is a physiological sensor of a performance measuring system for detecting a physiological signal in the user's body, the second electronic component is a heart rate transmitter of the performance measuring system, wherein the heart rate transmitter is configured to establish a wireless link for transmitting information, wherein the first electrically conductive layer is configured to transfer the physiological signal from the physiological sensor to the second electrically conductive layer and the second electrically conductive layer is configured to transfer the physiological signal to the heart rate transmitter; or wherein the first electronic component is a heart rate transmitter of a performance measuring system, wherein the heart rate transmitter is configured to establish a wireless link for transmitting information, wherein the second electronic component is a physiological sensor of a performance measuring system for detecting the physiological signal in the user's body, wherein the second electrically conductive layer is configured to transfer the physiological signal from the physiological sensor to the first electrically conductive layer and the first electrically conductive layer is configured to transfer the physiological signal to the heart rate transmitter.

10. The electronic device of claim 9, wherein the first electrically conductive layer and the second electrically conductive layer are configured for being sandwiched between the first magnetic layer and the second magnetic layer.

11. The electronic device of claim 9, further comprising a positioning structure for mutual positioning of the first electronic component and the second electronic component.

12. The electronic device of claim 9, wherein the first electrical component is a heart rate sensor comprising an elastic frame part and electrodes integrated in the elastic frame part, the electrodes being configured to be in electric contact with the user's thoracic area.

13. An electronic device comprising:
a first electronic component, which includes a first electrically conductive layer and a first magnetic layer, the first electrically conductive layer being coupled electrically and mechanically to the first electronic component, the first magnetic layer being configured to provide a mechanical coupling between a first connector part and a second connector part of a second electronic component based on the mutual magnetic attraction between the first magnetic layer and the magnetic layer of the second connector part of the second electronic component, the second electrically conductive layer being coupled electrically and mechanically to the second electronic component,
wherein the first electrically conductive layer is configured to provide an electrical connection between the first electrically conductive layer and the electrically conductive layer of the second electronic component based on said mutual magnetic attraction, thereby connecting the first electronic component and the second electronic component electrically and mechanically, wherein the first electronic component is a physiological sensor of a performance measuring system for detecting a physiological signal in the user's body, the second electronic component is a heart rate transmitter of the performance measuring system, wherein the heart rate transmitter is configured to establish a wireless link for transmitting information, wherein the first electrically conductive layer is configured to transfer the physiological signal from the physiological sensor to the second electrically conductive layer and the second electrically conductive layer is configured to transfer the physiological signal to the heart rate transmitter; or wherein the first electronic component is a heart rate transmitter of a performance measuring system, wherein the heart rate transmitter is configured to establish a wireless link for transmitting information, wherein the second electronic component is a physiological sensor of a performance measuring system for detecting the physiological signal in the user's body, wherein the second electrically conductive layer is configured to transfer the physiological signal from the physiological sensor to the first electrically conductive layer and the first electrically conductive layer is configured to transfer the physiological signal to the heart rate transmitter.

14. The electronic device of claim 13, wherein the first electrically conductive layer is configured for being sandwiched between the first magnetic layer and the second electronic device.

15. The electronic device of claim 13, wherein the first electronic component includes a positioning structure for mutual positioning of the first electronic component and the second electronic component.

16. The electronic device of claim 13, wherein the first electrical component is a heart rate sensor comprising an elastic frame part and electrodes integrated in the elastic frame part, the electrodes being configured to be in electric contact with the user's thoracic area.

17. A garment comprising a connector for coupling the garment mechanically and electrically, the connector comprising:
a first connector part coupled electrically and mechanically to a first electronic component, the first connector part including a first electrically conductive layer and a first magnetic layer, the first magnetic layer being configured to provide a mechanical coupling between the first connector part and a second connector part based on the mutual magnetic attraction between the first magnetic layer and a magnetic layer of the second connector part, the second connector part being coupled electrically and mechanically to a second electronic component,
the first electrically conductive layer being configured to provide an electrical connection between the first electrically conductive layer and an electrically conductive layer of the second connector part based on said mutual magnetic attraction, thereby connecting the first electronic component and the second electronic component electrically and mechanically, wherein the first electronic component is a physiological sensor of a performance measuring system for detecting a physiological signal in the user's body, the second electronic component is a heart rate transmitter of the performance measuring system, wherein the heart rate transmitter is configured to establish a wireless link for transmitting information, wherein the first electrically conductive layer is configured to transfer the physiological signal from the physiological sensor to the second electrically conductive layer and the second electrically conductive layer is configured to transfer the physiological signal to the heart rate transmitter; or wherein the first electronic component is a heart rate transmitter of a performance measuring system, wherein the heart rate transmitter is configured to establish a wireless link for transmitting information, wherein the second electronic component is a physiological sensor of a performance measuring system for detecting the physiological signal in the user's body, wherein the second electrically conductive layer is configured to transfer the physiological signal from the physiological sensor to the first electrically conductive layer and the first electrically conductive layer is configured to transfer the physiological signal to the heart rate transmitter.

18. The garment of claim 17, wherein the first electrical component is a heart rate sensor comprising an elastic frame part and electrodes integrated in the elastic frame part, the electrodes being configured to be in electric contact with the user's thoracic area.

19. A physiological sensor comprising a connector for coupling the physiological sensor mechanically and electrically, the connector comprising:

a first connector part coupled electrically and mechanically to a first electronic component, the first connector part including a first electrically conductive layer and a first magnetic layer, the first magnetic layer being configured to provide a mechanical coupling between the first connector part and a second connector part based on the mutual magnetic attraction between the first magnetic layer and a magnetic layer of the second connector part, the second connector part being coupled electrically and mechanically to a second electronic component, the first electrically conductive layer being configured to provide an electrical connection between the first electrically conductive layer and an electrically conductive layer of the second connector part based on said mutual magnetic attraction, thereby connecting the first electronic component and the second electronic component electrically and mechanically, wherein the first electronic component is a physiological sensor of a performance measuring system for detecting a physiological signal in the user's body, the second electronic component is a heart rate transmitter of the performance measuring system, wherein the heart rate transmitter is configured to establish a wireless link for transmitting information, wherein the first electrically conductive layer is configured to transfer the physiological signal from the physiological sensor to the second electrically conductive layer and the second electrically conductive layer is configured to transfer the physiological signal to the heart rate transmitter; or wherein the first electronic component is a heart rate transmitter of a performance measuring system, wherein the heart rate transmitter is configured to establish a wireless link for transmitting information, wherein the second electronic component is a physiological sensor of a performance measuring system for detecting the physiological signal in the user's body, wherein the second electrically conductive layer is configured to transfer the physiological signal from the physiological sensor to the first electrically conductive layer and the first electrically conductive layer is configured to transfer the physiological signal to the heart rate transmitter.

20. The physiological sensor of claim 19, wherein the first electrical component is a heart rate sensor comprising an elastic frame part and electrodes integrated in the elastic frame part, the electrodes being configured to be in electric contact with the user's thoracic area.

* * * * *